United States Patent [19]
Kellner et al.

[11] Patent Number: 5,922,609
[45] Date of Patent: Jul. 13, 1999

[54] METHOD FOR INFRARED-OPTICAL DETERMINATION OF THE CONCENTRATION OF AT LEAST ONE CHEMICAL ANALYTE IN A LIQUID SAMPLE

[75] Inventors: Robert Kellner, deceased, late of Vienna, by Wolfgang Reinold, legal representative; Max Lippitsch, Graz, both of Austria

[73] Assignee: Anton Paar GmbH, Graz, Austria

[21] Appl. No.: 08/965,230

[22] Filed: Nov. 6, 1997

[30] Foreign Application Priority Data

Nov. 6, 1996 [AT] Austria ................................. 1940/96

[51] Int. Cl.⁶ ................................................. G01N 33/00
[52] U.S. Cl. ...................... 436/103; 436/100; 436/129; 436/164
[58] Field of Search ................................. 436/100, 103, 436/164, 129

[56] References Cited

U.S. PATENT DOCUMENTS

| | | | |
|---|---|---|---|
| 3,125,419 | 3/1964 | Geld et al. | 436/100 |
| 3,795,484 | 3/1974 | Daly et al. | 436/164 |
| 4,599,316 | 7/1986 | Hahn et al. | 436/103 |
| 5,212,099 | 5/1993 | Marcus | 436/164 |
| 5,252,486 | 10/1993 | O'Lear et al. | 436/103 |
| 5,310,526 | 5/1994 | Yalvac et al. | |
| 5,492,718 | 2/1996 | O'Neill et al. | 427/8 |
| 5,646,315 | 7/1997 | Schultz et al. | 549/554 |
| 5,783,251 | 7/1998 | Tomozawa et al. | 427/8 |

FOREIGN PATENT DOCUMENTS

| | | |
|---|---|---|
| 0265630 | 5/1988 | European Pat. Off. . |
| 19748849 A1 | 5/1998 | Germany . |
| 1521085 | 8/1978 | United Kingdom . |

OTHER PUBLICATIONS

International Publication No. WO 85/04478 to Pentti Niemelä et al. entitled, "Procedure for Measuring Contents of Hydrocarbons in Liquids Containing Such," dated Oct. 10, 1985.

Vonach, R.; Lendl, B.; and Kellner, R. "Modulation of the pH in the Determination of Phosphate with Flow Injection and Fourier Transform Infrared Detection." Analyst, 122, 525–530, Jun. 1997.

Daniel, T.B.; Scherson, D. A.; and Yeager, E. B. "Infrared Spectroscopic Determination of pH Changes in Diffusionally Decoupled Thin–Layer Electrochemical Cells." Anal. Chem. 62, 45–49, 1989.

Rudolph, W., and Steger, W. E. "Dissociation, Structure, and Rapid Proton Exchange of Phosphoric Acid in Dilute Aqueous Solutions. V. Vibrational Spectra of Phosphoric Acid." Z. Phys. Chem. (Munich) (1991), 172(1), 49–59.

Vonach, R.; Kellner, R.; and Lippitsch, M. "A Phosphate Sensor for Soft–Drinks Based on IR–Spectroscopy." Curr. Status Future Trends Anal. Food Chem., Proc. Eur. Conf. Food Chem., 8th (1995), vol. 3, 573–577.

Esteves da Silva, Joaquim; Machado, A.; and Oliveira, C. "Monitoring of Molecular Transformations in Acid–Base Reactions by Evolving Factor Analysis of Fourier Transform Infrared Spectral Data." Talanta, 43, 1443–1456, Sep. 1996.

Primary Examiner—Jill Warden
Assistant Examiner—Kevin P. Cannell
Attorney, Agent, or Firm—Watson Cole Grindle Watson, P.L.L.C.

[57] ABSTRACT

In a method for infrared-optical determination of the concentration of at least one chemical analyte in a liquid sample, where the liquid sample is passed through a measuring cell and irradiated with infrared radiation of a single narrow waverange and infrared absorption is measured, the analyte being determined is subject to a chemical reaction before measurement, which should leave the other components of the liquid sample unaffected, and the change in infrared absorption caused by the chemical reaction with the analyte is measured as a unique function of the analyte concentration to be determined.

20 Claims, 2 Drawing Sheets

METHOD FOR INFRARED-OPTICAL DETERMINATION OF THE CONCENTRATION OF AT LEAST ONE CHEMICAL ANALYTE IN A LIQUID SAMPLE

BACKGROUND OF THE INVENTION

This invention relates to a device and method for infrared-optical determination of the concentration of at least one chemical analyte in a liquid sample, where the liquid sample is passed through a measuring cell and irradiated with infrared radiation of a single narrow waverange and infrared absorption is measured.

Measuring substance concentrations is required in many fields of science and technology, such as chemistry, process-, manufacturing-, or medical engineering, analytical chemistry in ecology or food technology. For many analytes to be determined the infrared region of the spectrum offers characteristic absorption bands from whose intensities the analyte concentration may be determined in principle. Infrared spectrometers are expensive and complex devices, however, which are awkward to handle and ill-suited for on-line measurement in a production plant, for example. Moreover, the analyte is often provided at low concentration in a solvent which itself will absorb in the respective waverange. In aqueous solutions above all, the absorption of water will produce a dominant background signal in the entire infrared region. As a consequence, direct determination of the concentration will be difficult and inaccurate.

This problem may be solved by taking measurements at two wavelengths at least, one of which is chosen such that only the background absorption by the solvent is detected, whereas the other wavelength is within the absorption band of the analyte, thus covering analyte absorption and background absorption. The two wavelengths may be generated by separate radiation sources, or from the spectrum of a single broadband source by means of two band filters. The disadvantage of this method, however, is that the ratio of the intensities of the two wavelengths must be absolutely constant to prevent measuring errors. When two separate light sources are used, intensities will fluctuate independently of each other and a constant intensity ratio will be difficult to obtain, necessitating complex provisions for control. Even if a single source is used the intensity ratio will change along with changes in temperature and in the emission properties of the radiation source as well as the transmission properties of the band filters. Such a change again may be compensated only by monitoring and readjusting both intensities, which will entail considerable technical effort and financial expense.

DESCRIPTION OF THE PRIOR ART

In WO 85/04478 A1 a method is described in which the liquid to be measured is passed through a transparent cell and exposed to infrared radiation from a radiation source. The hydrocarbon concentration of the liquid is determined based on the difference in absorption of the liquid containing the hydrocarbons compared with the absorption of the pure liquid. Infrared absorption is measured in a preselected and comparatively large range of wavelengths corresponding to the range within which the hydrocarbon analyte contributes to the overall absorption. The degree to which the liquid contributes to absorption is measured outside of this range and the actual measurement value is obtained by forming the difference between the absorption values measured.

In EP 0 265 630 A2 an apparatus and method for chemical analysis of a liquid specimen are disclosed in this context, where a device for measuring light transmittance is provided, comprising a light source, a photodetector and a signal processor. In order to determine the concentration of a substance in the liquid the light source is covered with a reactant entering a chemical reaction with the sample analyte, light transmittance of the reactant being measured before and after sample contact. The reactant may be provided in a solid matrix, for example in the form of a test strip or similar such indicator means. The method is not suitable for on-line measurements in a production plant, however.

In U.S. Pat. No. 5,310,526 a chemical sensor is described, which comprises a measuring cell with two inlet openings, each of which is plugged by a porous stopper. Between the two stoppers a reaction chamber is formed, into which the sample is pressure-fed through one of the porous stoppers and a reactant is pressure-fed through the other one. The sample, or rather, the sample component being analyzed, reacts with the reactant and is detected by absorption spectroscopy. To improve the mixing of sample and reactant the reaction chamber is in contact with an ultrasound source. The reaction product is carried off through an outlet opening.

In GB 1 521 085 A a detector for an infrared analyzer is described, which is used to determine the concentration of a specific component in a liquid or gaseous specimen. A filter is placed between sample cell and radiation source, which transmits infrared radiation of a single narrow waverange.

SUMMARY OF THE INVENTION

It is an object of this invention to propose a simple method and apparatus for measuring substance concentrations by infrared-optical means, which avoid the disadvantages of the methods and devices referred to above, and are particularly well suited for on-line measurements in production plants.

According to the invention this object is achieved by subjecting the analyte to be determined to a chemical reaction prior to measurement, which has no influence on the other components of the liquid sample, and by measuring the change in infrared absorption effected by the chemical reaction with the analyte as unique function of the analyte concentration to be determined.

A device according to the invention for infrared-optical determination of the concentration of at least one chemical analyte in a liquid sample, comprising a measuring cell through which the sample liquid is passed and which is positioned in the radiation path between a radiation source supplying infrared radiation and a detector measuring the infrared absorption due to the analyte in the measuring cell—a filter being placed between measuring cell and radiation source, which will transmit infrared radiation of a single narrow waverange—, is characterized in that a reaction vessel is positioned upstream of the measuring cell, in which vessel the analyte may be treated in such manner that its absorption behavior will undergo a change.

The measuring principle proposed by the invention will now be explained by describing an advantageous embodiment of the invention, i.e., a device for measuring the concentration of phosphate in beverages. This application is of importance as phosphoric acid is added as an acidifier to a variety of beverages. In production control phosphate is frequently used as a reference substance in monitoring the correct formula of the beverage. In previous measurements the so-called molybdenum blue reaction has mainly been employed, which is time-consuming and unsuited for on-line control. Moreover, the method is inaccurate when used with strongly coloured beverages, since it is based on absorption measurement in the visible range of the spectrum.

BRIEF DESCRIPTION OF THE DRAWINGS

The invention will now be further described with reference to the accompanying drawings, in which.

DESCRIPTION OF PREFERRED EMBODIMENTS

Figure 1:
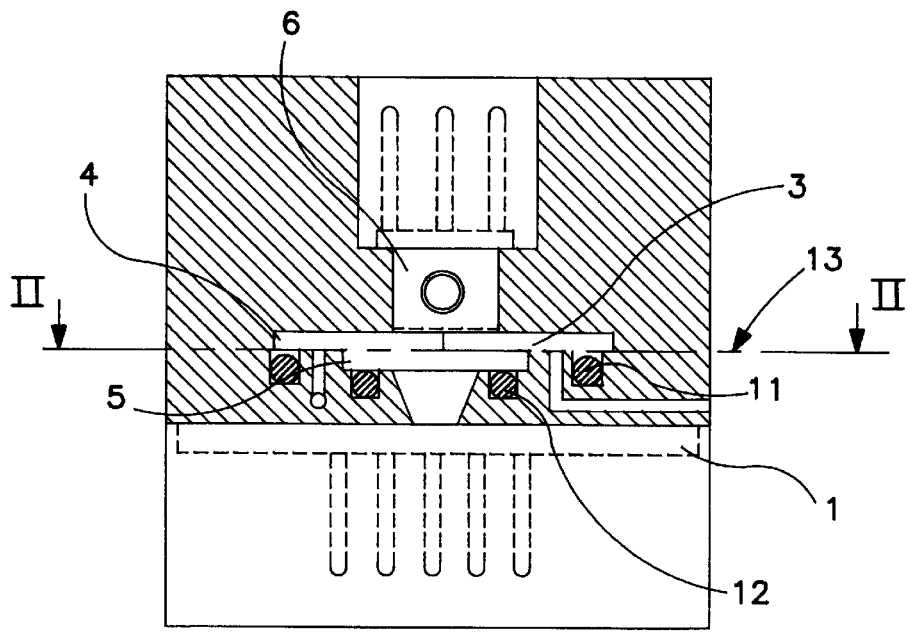
FIG. 1 and FIG. 2 are sectional representations of a device for implementation of the measuring method described by the invention.
Figure 2:
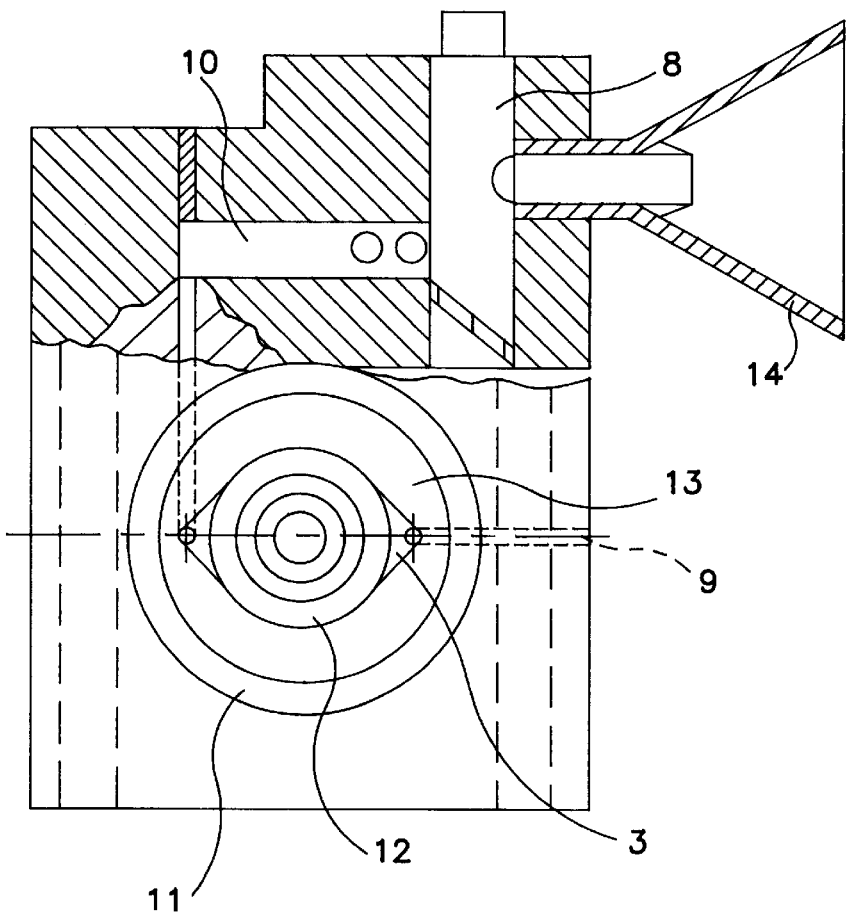
Figure 3:
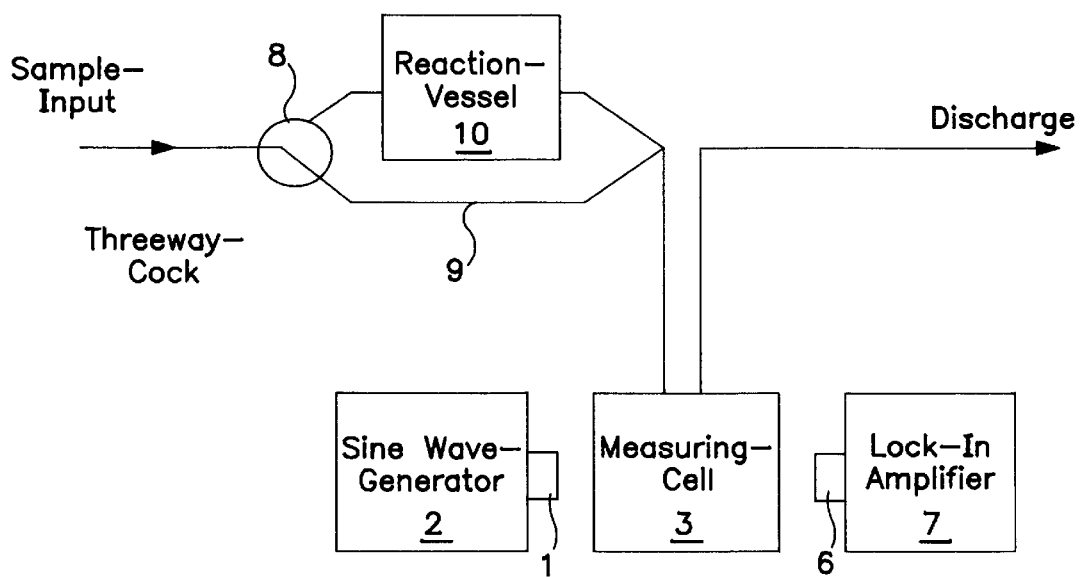
FIG. 3 is a schematical representation of the device according to the invention.

The radiation source used in FIGS. 1 to 3 is a thin-film radiator 1, which is stimulated to emit infrared radiation by means of a current flow supplied by a sine wave generator 2 and sine-modulated with a frequency f, the intensity of infrared emissions varying periodically with the same frequency. The beverage to be analyzed has a pH value in the acid range, i.e., phosphate is present almost exclusively in the form of $H_2PO_4$ or $H_3PO_4$ (single-charged phosphate or uncharged phosphoric acid), which is characterized by little or no absorption at the given wavelength. The infrared radiation emitted by the thin-film radiator 1 passes through a measuring cell 3 formed by two plane-parallel, infrared-transmitting filters 4 and 5. One of the two filters, 4, is configured as a narrow-band filter, whose transmission maximum coincides with the absorption band of $PO_4^{3-}$ (triple-charged phosphate; absorption maximum at a wave number of $1005\ cm^{-1}$). A pyroelectric detector 6 picks up the radiation energy passed by the filter, and converts it into a voltage signal. The signal, which is modulated with the frequency f, is detected by means of a lock-in amplifier 7. By turning a threeway cock 8 two different sample paths may be selected along which the liquid will flow to the measuring cell 3: either directly through branch line 9, in which instance the liquid will retain its original pH and contain no $PO_4^{3-}$ in the measuring cell 3, or through a reaction vessel 10, where its pH value will rise to >13.0 by reaction with sodium hydroxide solution, such that phosphate will be present almost exclusively in triple-charged form. If the cell 3 has a film thickness of 25 μm, absorption of the sample liquid will therefore change by 30 mA.U. for one gram of phosphate per liter. Suitable low-noise detectors will thus permit resolution of the concentration measurement to better than 1 mg/l, which will significantly exceeed the typical accuracy of the molybdenum blue method. The measuring cell is sealed by two O-rings 11 and 12; 13 refers to a teflon foil, whose thickness of 0.025 mm will define the film thickness of the cell 3. Via vessel 14 the reactant is fed to the reaction vessel 10.

The chemical influence modulating infrared absorption in this case is a change in pH. If this is only a change from the originally acid pH value to a pH between 9 and 11, the phosphate is present almost exclusively in double-charged form. In this instance measurements must be performed within the absorption band of this species ($1088\ cm^{-1}$); the device itself remains unchanged.

In another preferable embodiment of the invention this change in pH is achieved not by reaction with sodium hydroxide solution but with a solid ion exchanger with alkaline properties. Radiation source, measuring cell and detection unit remain the same as in the previous variant. Instead of the contact with the sodium hydroxide solution contact is established in the reaction vessel 10 with the solid ion exchanger, which will lead to an increase in pH.

According to the invention the desired change in pH towards the alkaline region of the scale could also be obtained by the addition of a buffer mixture, preferably $Na_2CO_3$, $NaHCO_3$.

Advantageous variants of the invention are suitable for measuring other acids, particularly organic acids. Citrate, for example, is preferably measured via infrared absorption at a wave number of $1570\ cm^{-1}$. In this region only the triple-charged form will absorb. In this instance the pH must be raised from about 2 to >9. Acetate may be measured at a wave number of $1250\ cm^{-1}$, the pH changing from 2 to >7. In measuring citrate and acetate the increase in pH once more may be effected by an alkaline solution, such as sodium hydroxide solution, or a solid, alkaline ion exchanger.

For further variants of the invention chemical processes other than changing the pH value may be utilized. By suitable choice of the wavelength and the chemical reaction to be used for measurement, a variety of analytes may thus be detected.

We claim:

1. A method for infrared-optical determination of the concentration of at least one chemical analyte in a liquid sample, comprising the steps of a) passing said liquid sample through a measuring cell, b) adding an acid, base, or buffer mixture to said liquid sample to cause a chemical reaction prior to measurement, which chemical reaction has no influence on other components of said liquid sample, said addition leading to a change in sample pH and a formation of differently charged forms of said analyte, which exhibit significant differences in infrared absorption measured as a unique function of said analyte concentration, c) irradiating said liquid sample with infrared radiation of a single narrow waverange and measuring infrared absorption, and d) calculating changes in infrared absorption effected by said chemical reaction with said analyte as a unique function of said analyte concentration.

2. A method according to claim 1, wherein for determination of the concentration of phosphoric acid in said liquid sample the absorption is measured at a wave number of $1005\ cm^{-1}$, and an alkaline solution is added to said liquid sample in step b) until sample pH rises into alkaline regions of about pH>13, at which value phosphate is present almost exclusively in the absorbing, triple-charged form.

3. A method according to claim 2, wherein said alkaline solution is a sodium hydroxide solution.

4. A method according to claim 1, wherein for determination of the concentration of phosphoric acid in said liquid sample the absorption is measured at a wave number of $1088\ cm^{-1}$, and an alkaline solution is added to said liquid sample in step b) until sample pH rises into alkaline regions of about pH=9–11, at which value phosphate is present almost exclusively in the absorbing double-charged form.

5. A method according to claim 4, wherein said alkaline solution is a sodium hydroxide solution.

6. A method according to claim 1, wherein for determination of the concentration of phosphoric acid in said liquid sample the absorption is measured at a wave number of $1088\ cm^{-1}$, and a buffer mixture is added to said liquid sample in step b) until sample pH rises into alkaline regions of about pH=9–11, at which value phosphate is present almost exclusively in the absorbing, double-charged form.

7. A method according to claim 6, wherein said buffer mixture is a mixture of $Na_2CO_3$ and $NaHCO_3$.

8. A method according to claim 1, wherein for determination of the concentration of citric acid in said liquid sample the absorption is measured at a wave number of 1570

$cm^{-1}$, and an alkaline solution is added to said liquid sample in step b) until sample pH rises into alkaline regions of about pH>9, at which value citrate is present almost exclusively in the absorbing, triple-charged form.

9. A method according to claim 8, wherein said alkaline solution is a sodium hydroxide solution.

10. A method according to claim 1, wherein for determination of the concentration of citric acid in said liquid sample the absorption is measured at a wave number of 1570 $cm^{-1}$, and a buffer mixture is added to said liquid sample in step b) until sample pH rises into alkaline regions of about pH>9, at which value citrate is present almost exclusively in the absorbing, triple-charged form.

11. A method according to claim 10, wherein said buffer mixture is a mixture of $Na_2CO_3$ and $NaHCO_3$.

12. A method according to claim 1, wherein for determination of the concentration of acetic acid in said liquid sample the absorption is measured at a wave number of 1250 $cm^{-1}$, and an alkaline solution is added to said liquid sample in step b) until sample pH rises into alkaline regions where acetic acid is present almost exclusively in the absorbing, single-charged form as acetate.

13. A method according to claim 12, wherein said alkaline solution is a sodium hydroxide solution.

14. A method according to claim 1, wherein for determination of the concentration of acetic acid in said liquid sample the absorption is measured at a wave number of 1250 $cm^{-1}$, and a buffer mixture is added to said liquid sample in step b) until sample pH rises into alkaline regions where acetic acid is present almost exclusively in the absorbing, single-charged form as acetate.

15. A method according to claim 14, wherein said buffer mixture is a mixture of $Na_2CO_3$ and $NaHCO_3$.

16. A method for infrared-optical determination of the concentration of at least one chemical analyte in a liquid sample, comprising the steps of
   a) passing said liquid sample through a measuring cell,
   b) subjecting said chemical analyte to be determined to a chemical reaction prior to measurement, which chemical reaction has no influence on other components of said liquid sample, said subjecting being contacting said sample with a solid alkaline ion exchanger to increase the sample pH into alkaline regions,
   c) irradiating said liquid sample with infrared radiation of a single narrow waverange and measuring infrared absorption, and
   d) calculating changes in infrared absorption effected by said chemical reaction with said analyte as a unique function of said analyte concentration.

17. A method according to claim 16, wherein for determination of the concentration of phosphoric acid in said liquid sample the absorption is measured at a wave number of 1005 $cm^{-1}$, and wherein sample pH rises into alkaline regions of about pH>13, at which value phosphate is present almost exclusively in the absorbing, triple-charged form.

18. A method according to claim 16, wherein for determination of the concentration of phosphoric acid in said liquid sample the absorption is measured at a wave number of 1088 $cm^{-1}$, and said sample is contacted with a solid, alkaline ion exchanger in step b), such that sample pH rises into alkaline regions of about pH=9–11, at which value phosphate is present almost exclusively in the absorbing, double-charged form.

19. A method according to claim 16, wherein for determination of the concentration of citric acid in said liquid sample the absorption is measured at a wave number of 1570 $cm^{-1}$, and wherein sample pH rises into alkaline regions of about pH>9, at which value citrate is present almost exclusively in the absorbing, triple-charged form.

20. A method according to claim 16, wherein for determination of the concentration of acetic acid in said liquid sample the absorption is measured at a wave number of 1250 $cm^{-1}$, and wherein sample pH rises into alkaline regions where acetic acid is present almost exclusively in the absorbing, single-charged form as acetate.

* * * * *